United States Patent [19]

Alberti et al.

[11] Patent Number: 5,133,857

[45] Date of Patent: Jul. 28, 1992

[54] SOLID-STATE SENSOR FOR THE DETERMINATION OF CONCENTRATION OF GASES WHICH CAN REACT WITH HYDROGEN

[75] Inventors: Giulio Alberti; Mario Casciola; Roberto Palombari, all of Perugia, Italy

[73] Assignee: Eniricherche S.p.A. and Snam S.p.A., Milan, Italy

[21] Appl. No.: 776,863

[22] Filed: Oct. 16, 1991

Related U.S. Application Data

[63] Continuation of Ser. No. 623,535, Dec. 7, 1990, abandoned.

[30] Foreign Application Priority Data

Dec. 12, 1989 [IT] Italy .................. 22663 A/89

[51] Int. Cl.[5] ............................ G01N 27/26
[52] U.S. Cl. ..................... 204/425; 204/412; 204/424; 204/421
[58] Field of Search .............. 204/268, 153.1, 424, 204/415, 153.22, 425, 412, 421, 153.18

[56] References Cited

U.S. PATENT DOCUMENTS

| | | | |
|---|---|---|---|
| 3,732,157 | 5/1973 | Dewitt | 204/268 |
| 4,226,692 | 10/1980 | Isenberg | 204/424 |
| 4,312,332 | 1/1982 | Zick | 204/415 |
| 4,707,244 | 11/1987 | Harmon, III et al. | 204/153.22 |
| 4,718,991 | 1/1988 | Yamazoe et al. | 204/424 |
| 4,879,005 | 11/1989 | Fray et al. | 204/153.1 |
| 4,976,991 | 12/1990 | Ammende et al. | 204/424 |

FOREIGN PATENT DOCUMENTS 0060944  9/1982  European Pat. Off.
0107279  5/1984  European Pat. Off.

OTHER PUBLICATIONS

Patent Abstracts of Japan, vol. 5, No. 182 (P-90)(854), Nov. 20, 1981 and JP-A-56 111 453 (Matsushita), Mar. 9, 1981.

Solid State Ionics, vol. 35, No. 1/2, Jul./Aug. 1989, pp. 153-156, G. Alberti, et al., "All Solid State Hydrogen Sensors Based on Pellicular A-Zirconium Phosphate as a Protonic Conductor", pp. 153, 154.

*Primary Examiner*—John Niebling
*Assistant Examiner*—Bruce Bell
*Attorney, Agent, or Firm*—Oblon, Spivak, McClelland, Maier & Neustadt

[57] ABSTRACT

A solid-state sensor for determining the concentration of gases which can react with hydrogen, in particular, of oxygen, which includes a solid-state proton conductor into contact: on the one side, with a reference electrode, constituted in its turn by a metal hydride or a metal alloy, and on the other side with an electrode which catalyses the reaction of the gas to be detected, with said sensor being connected with a power feed system which supplies current or voltage impulses, and with a system which detects the value of potential after each impulse.

8 Claims, 3 Drawing Sheets

SOLID-STATE SENSOR FOR THE DETERMINATION OF CONCENTRATION OF GASES WHICH CAN REACT WITH HYDROGEN

This application is a continuation of application Ser. No. 07/623,535, filed on Dec. 7, 1990, now abandoned.

BACKGROUND OF THE INVENTION

1. Field of the Invention

The present invention relates to a solid-state sensor for determining the concentration of gas species, in particular oxygen, which can react with hydrogen, which solid-stage sensor can also operate at room temperature.

2. Discussion of the Background

The determination of the oxygen content in a gas mixture or in liquids is an important problem from the industrial, biological, environmental, and still other, view points.

Very often, continuous monitoring is required, as in rivers, lakes or seas, to keep controlled the level of pollution caused by organic materials. Such a requirement can also occur in the case of biological liquids in general, or in gases generated by combustion processes, and other processes.

For that purpose, a method of voltametric type (Clark's method) is used [see: M. Kleitz, A. Pelloux, M. Gauthier in "Fast Ion Transport in Solids", page 69, Elsevier North Holland, Inc. (1979)].

During the past ten years, potentiometric systems were also introduced, which use a solid conductor for $O_2$, usually zirconium oxide doped with yttrium, which operate successfully only at temperatures higher than 400°-500° C. [see: E. Siebert, J. Fouletier, S. Vilminot "Solid State Ionics," 9 and 10 (1983) 1291].

Recently, attempts were carried out aiming at lowering the operating temperature of the potentiometric sensors, by studying other types of solid electrolytes [see: N. Miura, J. Hisamoto, S. Kuwata, N. Yamazoe "Chemistry Letters" (1987) 1477; T. Inoue, K. Eguchi, H. Arai "Chemistry Letters" (1988) 1939; S. Kuwata, N. Miura, Y. Yamazoe "Chemistry Letters" (1988) 1197].

SUMMARY OF THE INVENTION

It is an object of the present invention to provide a solid-state sensor for determining the concentration of gas species, in particular oxygen, which can react with hydrogen.

It is a further object of the present invention to provide a solid-state sensor which can operate at room temperature.

These and other objects are achieved by a solid-state sensor which detects the concentration of gases which can react with hydrogen, in particular oxygen, which includes a solid-state proton conductor, a reference electrode disposed on a first side of the conductor comprised of a metal hydride or a metal alloy, and a catalyzing electrode disposed on a second opposing side of the proton conductor which catalyzes a reaction with hydrogen of the gas to be detected, and an auxiliary electrode disposed on the first side of the solid-state proton conductor adjacent to the reference electrode, wherein a voltage or current impulse is applied to the auxiliary electrode using a power feed system and a value of potential of the reference electrode is detected after each impulse signal using a measuring system.

The solid-state conductor may be selected from the group consisting of uranyl hydrogen phosphate, antimonic acid, phosphomolybdic acid, zirconium hydrogen phosphate and an organic polymer containing acidic groups; the reference electrode may be selected from titanium hydride and zirconium hydride; the catalyzing electrode is composed of a noble metal, which may be platinum or palladium; and the auxiliary electrode is composed of a metal hydride or a metal alloy.

BRIEF DESCRIPTION OF THE DRAWINGS

A more complete appreciation of the invention and many of the attendant advantages thereof will be readily obtained as the same becomes better understood by reference to the following detailed desecration when considered in connection with the accompanying drawings, wherein.

DETAILED DESCRIPTION OF THE PREFERRED EMBODIMENTS

Figure 1:
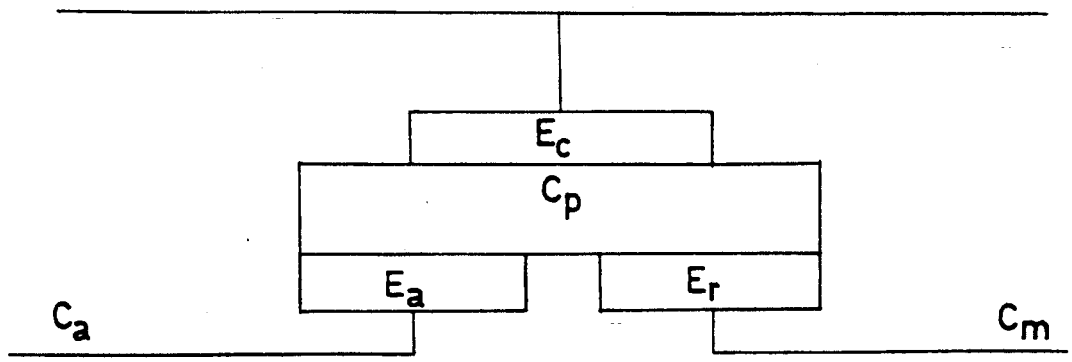
FIG. 1 is a schematic diagram of the solid-state sensor accord to the invention.

The present Application surprisingly found a new sensor which makes it possible, also operating at room temperature, to detect those gases which react with hydrogen, by detecting the production of hydrogen on the sensor electrode.

The solid-state sensor according to the present invention, for determining the concentration of gases which can react with hydrogen, in particular oxygen, is essentially constituted by a solid-state proton conductor into contact: on the one side, with a reference electrode, constituted a metal hydride or a metal alloy, and on the other side with a metal which catalyzes the reaction with the hydrogen of the gas to be detected, with said sensor being connected with a power feed system which supplies current or voltage impulses, and with a system which detects the value of potential after each impulse.

As the proton conductor, one already known from literature can be used such as, e.g., uranyl hydrogen phosphate, antimonic acid, phosphomolybdic acid, zirconium hydrogen phosphate, zirconium triphosphate and its forms doped with silicates, such as $H_3Zr_2PO_4(SiO_4)_2$ and organic polymers containing acidic groups, such as —COOH, —$SO_3$ (for example, NAFION or IONAC membranes).

Zirconium hydrogen phosphate may preferably be used in film or membrane form, as disclosed in U.S. patent application Ser. No. 07/312060.

The coating of the reference electrode with such films or membrane can be carried out as disclosed in above said patent application.

Since very thin, compact films (thickness less than 0.1 mm) can be obtained, the electrical resistance of the system is appreciably reduced. Furthermore, such a proton conductor is suitable for uses at room temperature and at higher then room temperatures, up to a maximum value of 350°-400° C., beyond which the acidic groups

—P—OH condense to yield pyrophosphate.

As reference electrodes, various metals, or metal alloys can be used, which form hydrides. Titanium and zirconium hydrides are preferred. Owing to the low conductivity of zirconium hydride at room temperature, said hydride should be preferably used at temperatures higher 100° C. by electrolytic way.

The reference electrode of titanium or zirconium hydride can be prepared, e.g., by heating a temperatures comprised within the range of from 400° to 700° C. and for a time of from 2 to 10 hours, a titanium or zirconium sheet (having a thickness of from 0.25 to 1.0 mm) in the presence of hydrogen gas as disclosed in U.S. patent application Ser. No. 07/312,060. The preparation of the reference electrode can be carried out by electrolytic route as well.

As catalyzing electrodes, the metals known from the prior art can be used. Among them, platinum and palladium are preferred. The electrode is preferably given the shape of a net or of a thin wire (0.1–0.5 mm) wound to give a flat and thin spiral. Also a platinum-coated metal can be used, on condition that the surface is not excessively porous.

The sensor may be completed with an auxiliary electrode to which the pulsed current or the pulsed voltage is applied.

In such a way, one can prevent the pulsed current from also flowing through the reference electrode.

The auxiliary electrode can be constituted by a metal hydride and such a hydride can be the same as used for the reference electrode: titanium hydride and zirconium hydride are preferred.

From a theoretical view point, the auxiliary electrode is liable to lose its hydrogen content during sensor operation.

On considering that through such an electrode extremely small current amounts flow, compared to the amount of hydrogen contained in the metal hydride, no drawbacks are expected to occur even after several years of operation.

If through the feed circuit a pulsed current flows, the impulse length can be of the order of from 10 to 100 milliseconds, while the time interval between two consecutive impulses can be of the order of from 1 to 10 seconds. During the application of an impulse, the auxiliary electrode operates as the anode. The hydrogen contained in the metal hydride flows through the proton conductor as H+ and an equivalent amount of protons is reduced at the catalyzing electrode, which operates as the cathode. The used current can be of the order of from 0.1 to 1.0 microamperes, depending on the surface-area of the electrode used. The width of the impulse is kept constant.

The potential of the sensor is determined after each current impulse. It is of course pulsed, and therefore can be filtered or, even better, it can be measured during a short time, of the order of one second, for example by a sample-hold system, before the successive impulse is applied.

The present Applicant found that the measured potential value is a function of O2 partial pressure according to the following equation:

$$E = a + b \log PO_2 \qquad (1)$$

in which:
  a is a constant depending on the reference potential and on the operating conditions, such as current intensity, impulses frequency, and so on;
  b is a constant of the order of 100 mV, influenced by the operating conditions as well.

The range of validity of equation (1) was determined by performing exponential dilutions of air in a stream of nitrogen flowing at a constant flow rate. A linear behavior was found to exist down to concentrations of O2 of the order of some per million parts, In FIG. 1 a sensor with an auxiliary electrode is schematically shown. In the figure:
  $C_a$ = pulsed-power feed circuit
  $C_m$ = measurement circuit
  $E_c$ = catalyzing electrode
  $E_r$ = reference electrode
  $E_a$ = auxiliary electrode
  $C_p$ = proton conductor.

Some examples are given now, the purpose of which is of better illustrating the present invention. In no way shall such examples be construed as being limitative of the same invention.

EXAMPLES

Example 1

A sensor constituted by: zirconium phosphate in film form (thickness 0.1 mm) as the proton conductor, titanium hydride as the reference electrode and platinum as the catalyzing electrode, operating under the following experimental conditions: temperature 20° C., feed with current impulses of 1 microampere, of 100 milliseconds of length and with a period of 10 seconds, measurements of potential carried out with a delay of 8 s after the impulse, was used to measure the content of O2 in air and in nitrogen-air mixtures with a relative humidity close to 100%.

Figure 2:
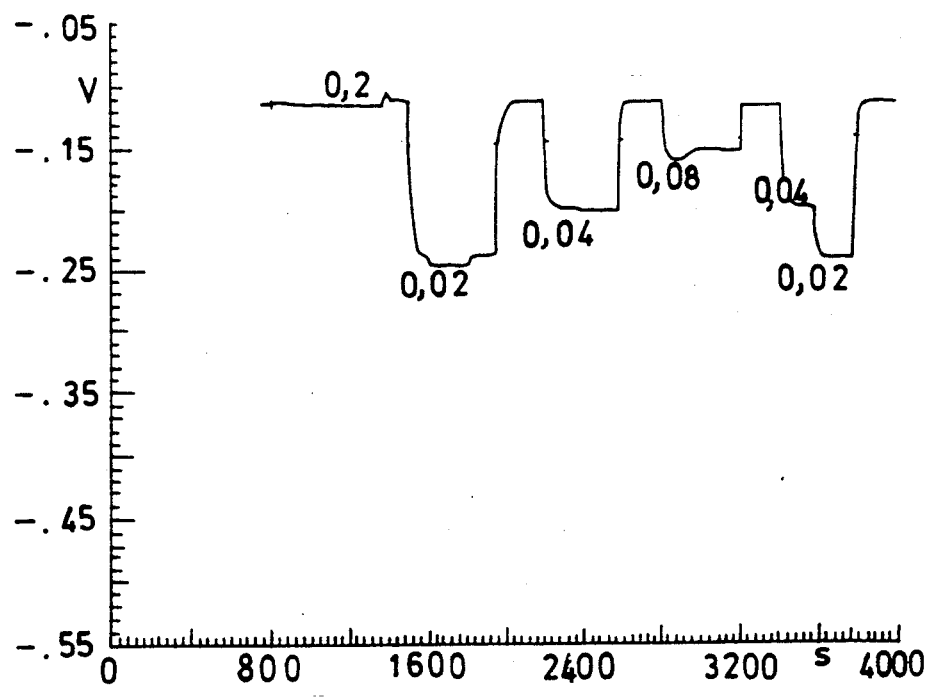
FIG. 2 is a graph showing the response of the sensor according to the invention at various partial pressures of oxygen.

The results, reported in the chart of FIG. 2, show the response reproducibility and velocity of the sensor at various partial pressures of O2 (indicated in the figure).

EXAMPLE 2

A sensor according to Example 1, operating under the same experimental conditions except current being of 0.5 microamperes, was used to measured the content of oxygen in oxygen-nitrogen mixtures.

For that purpose, an exponential-dilution system was used; oxygen, contained at the initial concentration $C_0$ inside a vessel of known volume V, was diluted by nitrogen fed at a constant flow-rate F. Oxygen leaves the vessel at a concentration C depending on time according to the equation $$\ln C = \ln Ce - Ft/V$$

Since the potential depends on O2 concentration according to a logarithmic relation, one should expect a linear decrease of potential with time.

Figure 3:
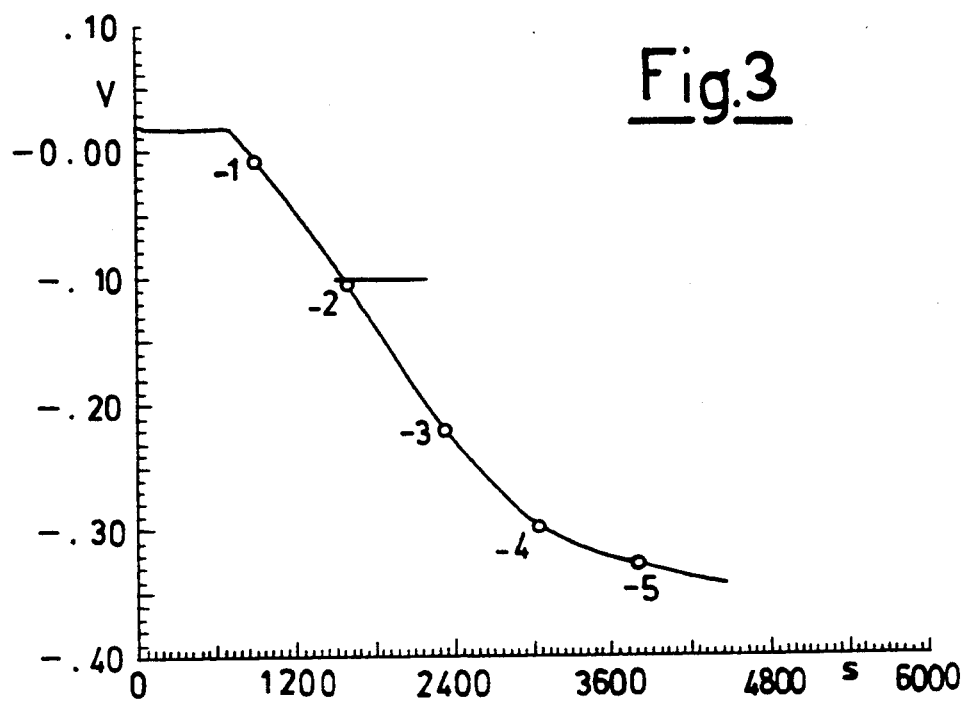
FIG. 3 is a graph of the responses of the sensor according to the invention to different oxygen partial pressures.

FIG. 3 shows the response of the sensor with varying times and varying oxygen concentrations (the numerical values reported in the figure are the logarithm of $O_2$ partial pressures). The potential decrease is in perfect agreement with the expected trend.

EXAMPLE 3

A sensor according to Example 1, operating under the following experimental conditions: temperature 40° C., impulse current b 0.3 microamperes, impulse lengths of 10 millisecond, period 10 s, potential measurement delay 8 seconds, was used to measure the content of $O_2$ in mixtures with nitrogen, by the exponential-dilution system.

Figure 4:
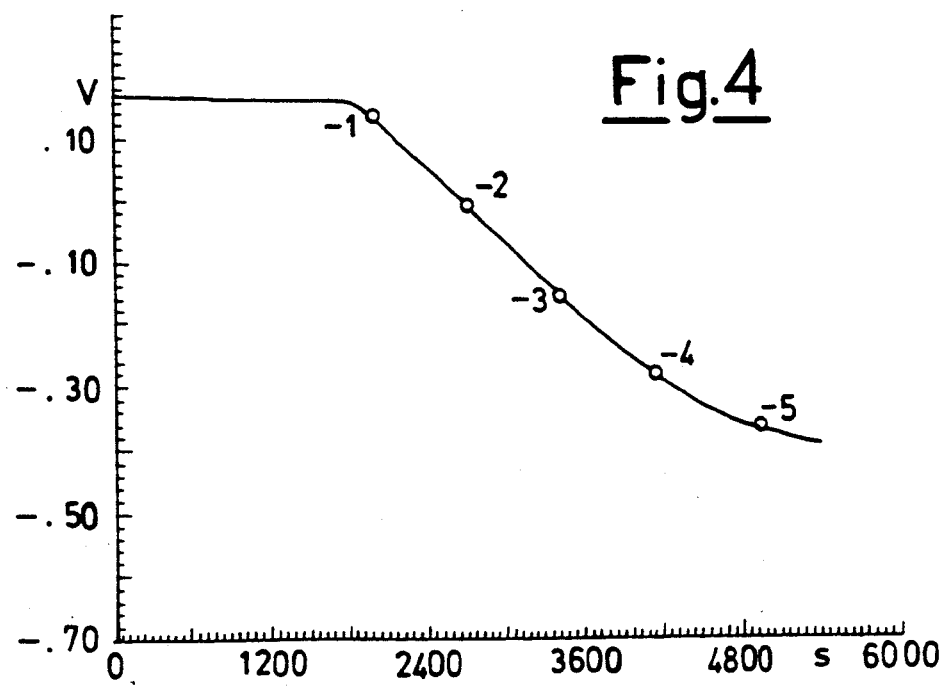
FIG. 4 is a graph of the response of the sensor according to the invention to different oxygen partial pressures.

The response of the sensor to $O_2$ concentrations over time is reported in FIG. 4 (the numerical values reported in the figure are the logarithm of $O_2$ partial pressures).

EXAMPLE 4

A sensor according to Example 1, but of the doubleelectrode type, i.e., equipped with a $TiH_x$ blade acting as the reference electrode-auxiliary electrode, was tested at 80° C. with humidified gases at room temperature.

Figure 5:
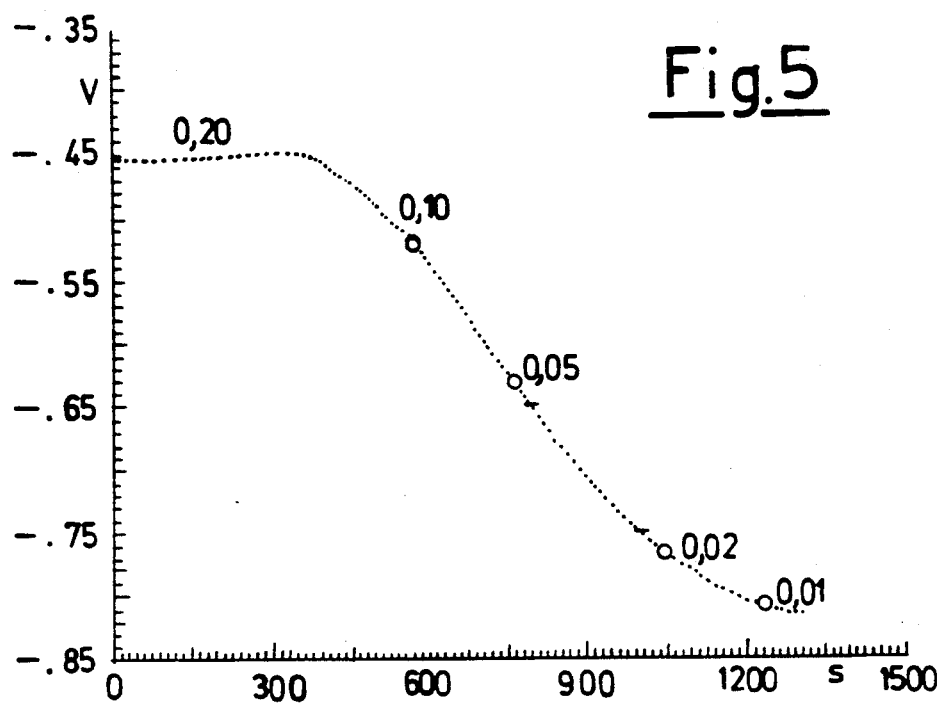
FIG. 5 is a graph of the response of the sensor according to the invention as a function of partial pressure of oxygen.

The operating conditions were: current of 0.10 microamperes, impulse length of 10 milliseconds, period of 10 seconds, potential measurement delay 8 seconds. The response of the sensor as a function of time and of the partial pressure of $O_2$, obtained by exponential dilution, is illustrated in FIG. 5.

EXAMPLE 5

A sensor analogous to that of Example 1, except the proton conductor being constituted by a membrane of NAFION (of 0.1 mm of thickness) operating under the experimental conditions of Example 1 except current intensity, which was of 0.3 microamperes, was used to measure the content of $O_2$ in mixtures with nitrogen.

Figure 6:
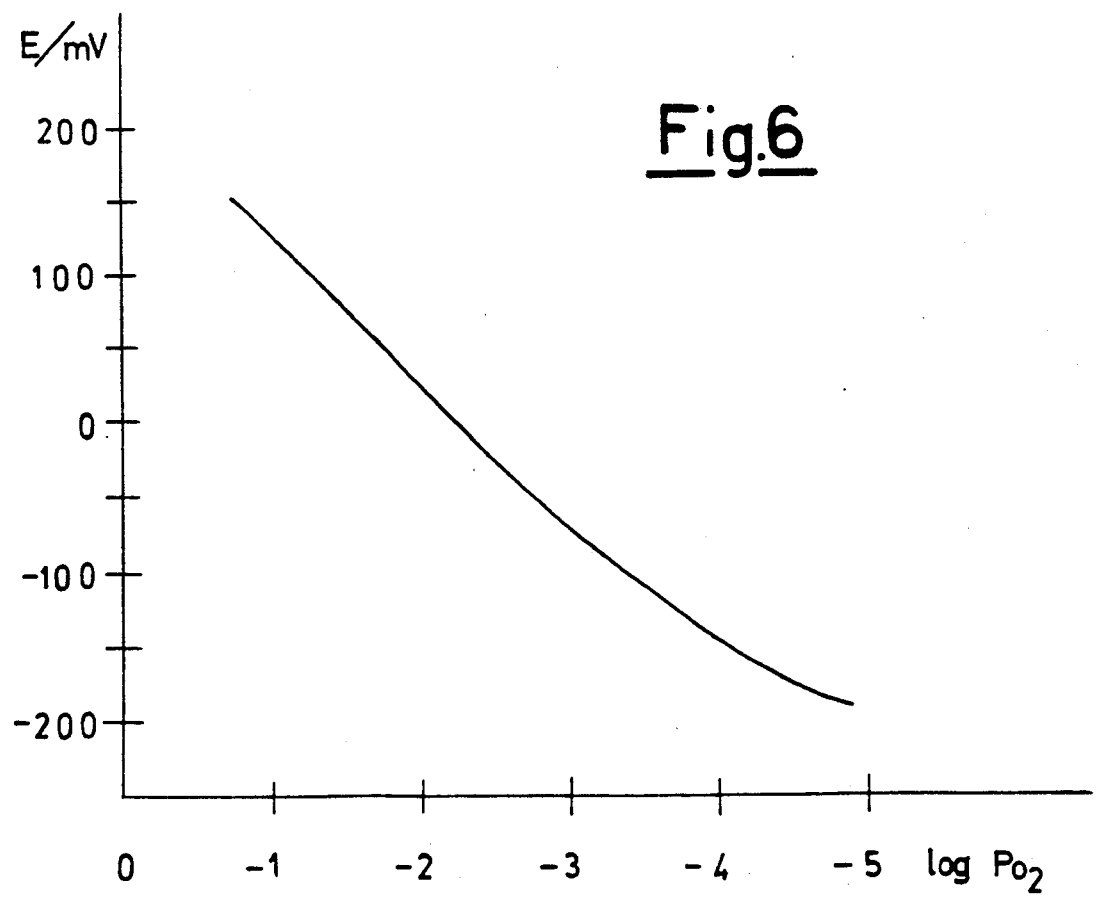
FIG. 6 is a grape illustrating the dependence of the potential produced by the sensor according to the invention as a function of partial pressure of oxygen.

The chart report in FIG. 6 shows the dependence of the potential reading on the logarithm of the partial pressure of $O_2$.

We claim:

1. A solid-state sensor for determining a concentration of gases which can react with hydrogen, in particular oxygen, comprising:
   a solid-state proton conductor;
   a reference electrode, disposed on a first side of said conductor, composed of a metal hydride or a metal alloy;
   a catalyzing electrode, disposed on a second side of said conductor opposing said first side, which catalyzes a reaction with hydrogen or a gas to be detected; and
   an auxiliary electrode disposed on said first side of said conductor;
   wherein said auxiliary electrode is supplied with a current or voltage impulse using a power feed system, and a potential of said reference electrode is measured after each of said impulses using a measuring system.

2. Sensor according to claim 1, in which the solid-state conductor for protons is selected from the group consisting of uranyl hydrogen phosphate, antimonic acid, phosphomolybdic acid, zirconium hydrogen phosphate and the organic polymers containing acidic groups.

3. Sensor according to claim 2, in which the zirconium hydrogen phosphate is in film or membrane form.

4. Sensor according to claim 1, in which the reference electrode is selected from titanium hydride and zirconium hydride.

5. Sensor according to claim 1, in which the catalyzing electrode is a noble metal.

6. Sensor according to claim 5, in which the noble metal of the catalyzing electrode is selected from platinum and palladium.

7. Sensor according to claim 6, in which the auxiliary electrode is a metal hydride or a metal alloy.

8. Sensor according to claim 7, in which the hydride of the auxiliary electrode is selected from titanium hydride and zirconium hydride.

* * * * *